(12) United States Patent
Lopez-Belmonte Encina et al.

(10) Patent No.: US 11,548,311 B2
(45) Date of Patent: Jan. 10, 2023

(54) DEVICE AND PROCEDURE FOR THE IDENTIFICATION OF PHARMACEUTICAL CONTAINERS

(71) Applicant: ROVI PHARMA INDUSTRIAL SERVICES, S.A.U., Madrid (ES)

(72) Inventors: Javier Lopez-Belmonte Encina, Madrid (ES); Jose Cristobal Gil, Madrid (ES); Cristina Casado Urtiaga, Madrid (ES)

(73) Assignee: ROVI PHARMA INDUSTRIAL SERVICES, S.A.U., Madrid (ES)

( * ) Notice: Subject to any disclaimer, the term of this patent is extended or adjusted under 35 U.S.C. 154(b) by 126 days.

(21) Appl. No.: 17/116,676

(22) Filed: Dec. 9, 2020

(65) Prior Publication Data

US 2021/0125014 A1 Apr. 29, 2021

Related U.S. Application Data

(63) Continuation-in-part of application No. PCT/ES2019/070435, filed on Jun. 21, 2019.

(30) Foreign Application Priority Data

Jun. 22, 2018 (ES) .............................. ES201830632

(51) Int. Cl.
| | |
|---|---|
| *G06K 19/06* | (2006.01) |
| *B42D 25/387* | (2014.01) |
| *B41J 3/407* | (2006.01) |
| *G16H 20/10* | (2018.01) |
| *G06K 7/10* | (2006.01) |

(52) U.S. Cl.
CPC .......... *B42D 25/387* (2014.10); *B41J 3/4073* (2013.01); *G06K 7/10732* (2013.01); *G06K 19/0614* (2013.01); *G16H 20/10* (2018.01)

(58) Field of Classification Search
CPC . G06K 7/10732; G06K 19/0614; G16H 20/10
USPC ....................................................... 235/385
See application file for complete search history.

(56) References Cited

U.S. PATENT DOCUMENTS

| | | | |
|---|---|---|---|
| 5,837,042 A | 11/1998 | Lent et al. | |
| 9,378,445 B2 | 6/2016 | Stuck et al. | |
| 9,662,920 B2 | 5/2017 | Kozee et al. | |
| 2007/0210164 A1* | 9/2007 | Conlon ................. | G06Q 10/08 235/491 |

FOREIGN PATENT DOCUMENTS

| | | |
|---|---|---|
| DE | 202008018588 U1 | 3/2016 |
| WO | 2011135398 A1 | 11/2011 |
| WO | 2017048499 A1 | 3/2017 |

* cited by examiner

*Primary Examiner* — Jamara A Franklin
(74) *Attorney, Agent, or Firm* — Innovar, L.L.C.; Rick Matos

(57) ABSTRACT

An identification device and procedure for pharmaceutical containers comprising at least one means of marking at least one secured identification code on each of the containers, characterised in that the device comprises at least one inkjet system configured to print the identification code on at least one surface of the moving container with at least one ink which exhibits visible fluorescence when radiated with ultraviolet (UV) radiation, and whose drying time is 1 to 3 seconds or less than about 3 seconds.

24 Claims, 3 Drawing Sheets

DEVICE AND PROCEDURE FOR THE IDENTIFICATION OF PHARMACEUTICAL CONTAINERS

CROSS-REFERENCE TO EARLIER FILED APPLICATIONS

The present application claims the benefit of and is a continuation-in-part of international application PCT/ES2019/070435 filed Jun. 21, 2019, which claims the benefit of Spanish application No. P201830632 filed Jun. 22, 2018, the entire disclosures of which are hereby incorporated by reference.

FIELD OF THE INVENTION

The present invention belongs to the field of processes for the marking of pharmaceutical containers, more specifically pharmaceutical containers of small dimensions such as syringes, cartridges or vials. The present invention relates to a device for the identification of the same, likewise to a procedure for the performance of said identification, enabling the signage and marking of said containers with security ink, thus preventing errors in the identification, serialization and traceability of the same.

BACKGROUND OF THE INVENTION

Currently, the pharmaceutical industry has problems when identifying the drugs existing on the market. This generates two fundamental problems, the first being the possible occurrence of errors during the manufacture and packaging when identifying the content of the container for various reasons, such as presenting an active ingredient or excipient which is different from that indicated on the container, the batch and/or expiration date being different, or having a different concentration, etc. The second problem is that counterfeit drugs may be found in the market. Both problems require an identification system enabling the individual tracing and serializing of the products in order to prevent disruptions in the safety and suitability of the drugs and other pharmaceutical products. This would have a beneficial impact on public health and on the rational use of medicines.

To overcome the first problem mentioned, that is, the possible occurrence of errors during the manufacturing process itself in the identification of the content of a drug, it is necessary to achieve a system enabling the marking on the body of the container holding the same, without interfering with the content, thus to ensure the suitability and standard of quality of the drug. Furthermore, it is important that this method or system should be performed during the manufacturing process itself or during the filling of the containers, thus to ensure a secure invisible marking and identification system which can be executed at any stage of the production process, even for containers intended for clinical trials, which do not bear a label.

In this sense, it must be borne in mind that the production of drugs which are packaged in containers of small dimensions entails a series of stages of packing and packaging, from the preparation and formulation of the product contained to its distribution in the market. Some of these stages, including but not limited thereto, are as follows:

Formulation
The filling, packing and capping of the containers
The inspection of the full or empty containers
Final sterilisation in the autoclave
The attachment of the plunger and labelling of the containers
The attachment of the safety device or back-stop (optional)
Blister packaging
Packing and marking of the variable data and/or serialisation
Boxing, etc.

Some products also require refrigerated storage between these stages (process steps).

Each of these stages is generally performed in different items of equipment with some distance between items. It is therefore necessary to transport the containers (usually syringes or cartridges), normally on trays, after each of the stages for their transfer to the room where the next stage is to be performed, it being possible that said containers may remain stored during a period of time, as according to the availability of the product filling or packaging lines, it is possible that the entire process may not be executed continuously.

Although the trays on which they are stored must be appropriately identified, it is not until they are labelled that the pharmaceutical containers have any real identification concerning the batch to which they belong and/or their packaging code, and consequently, any information on the product contained therein. This means that the possibility exists that cases of cross-contamination might occur.

For this reason, it is necessary to find a marking device and procedure which can be used on both types of containers (both those made of glass and of other materials such as cyclopolyolefin or other plastic materials), for the containers to be thus correctly identified from the moment they leave the packaging or filling stage to the next stage of the filling or packaging process.

With regard to the second problem described, that is, the existence of the possibility of finding counterfeit drugs in the market; a counterfeit drug being understood to be any drug whose presentation is forged regarding its identity, including the container, the labelling, name, composition or concentration regarding any of its components, including excipients, and the dosage of said components; with regard to its origin, including manufacturer, country of manufacture, country of origin and the owner of the marketing authorisation; also with regard to its history, including the records and documents concerning the distribution channels employed.

It should be highlighted that over the past few years there has been an alarming increase detected worldwide in counterfeit drugs with regard to their identity, history or origin. These drugs generally contain low-quality or false components or may even be toxic to health, or possibly they may or may not contain components, including active ingredients, where the content or the dosage is incorrect. Therefore, the existence of counterfeit drugs in the market is a threat to patient safety.

To act against the counterfeiting of drugs, several measures have been implemented, such as serialization or marking and traceability. Serialization is known as the attaching of unique product identification codes to the individual containers of all pharmaceutical material. On the other hand, traceability is the most efficient tool to monitor the transactions of drugs in real time, to verify the origin of the same, and to record the history of locations and transfers throughout the distribution chain. However, currently this serialization and traceability is performed either on the label or on the pharmaceutical package (that is, on paper or card), and not directly on the body of the containers, such as the syringes or cartridges containing the active ingredient, excipient or drug, these being made of plastic or glass and of various sizes.

This initiative is currently gaining importance thanks to European Directive no. 2016/161, by which the European Union has implemented certain mechanisms to fight the counterfeiting of drugs and the threat entailed thereby to Public Health, and which is mandatory for the pharmaceutical sector as from 2019.

For this reason, serialization and traceability on the body of the container itself has become necessary, to enable its individual identification throughout all the stages of the production process (from the moment when it is packed until it reaches the patient), thus ensuring the correct identification of the same, enabling the immediate detection of errors.

Among the systems described in the state of the art, there currently exist in the market different types of technology to execute the marking and identification of the containers. Principally, of note are the printing with ink on the labels and on the packages, and the direct marking of the container, but using a laser system which generates a wear of varying depth on the surface of the containers.

The printing systems currently used for labels and packages are inkjet printing systems and indirect thermal transfer printing systems (which apply heat to the printheads and transfer the material to be printed to the support by direct contact (label or package)); or direct thermal transfer printing, where direct contact is required between the printhead and the support, which is darkened by the heat.

On the other hand, if a laser-type marking is used, this enabling the direct marking of the container, an engraving of varying depth is generated on the body of the container, causing microcracks in the same which weaken the surface of the container to a point that, depending on the material of the latter, might jeopardize the resistance and integrity of the same. This causes a high rate of rejection of containers filled in a production process such as that described in the present invention, as on the one hand, the containers are friable (for example, glass syringes), and on the other, they are filled at high speed, which causes collisions between the same, and finally, they are of a small size, which causes the marking in question to occupy a considerable amount of the specific surface of the container, thus representing a considerable breaking point of the same (for example, it is not the same to mark a wine bottle with a two-dimensional data code measuring 5×5 mm as to mark a syringe).

It is therefore necessary to achieve a device enabling the individual marking of the body of a container, which can be adapted to any production process and at any stage of the filling of pharmaceutical containers, and which does not jeopardize the strength and integrity of the same.

As examples of the state of the art, the following reference documents may be mentioned: ES25311415, WO2017/048499 A1, U.S. Pat. Nos. 9,662,920 B2, 5,837,042 A and 9,378,445 B2, wherein marking procedures are described.

ES25311415 discloses a method for marking a transparent container with a transparent wall, comprising the stages consisting of the application of at least one smear of ink on an external surface of said transparent wall, heating said transparent wall and engraving a data matrix on the ink smear on said transparent wall. This document discloses the importance, on the one hand, of determining where a container has come from, what it contains, and the intended use of the same; and on the other hand, that this information cannot be forged. They therefore state the need for the marking of containers such as syringes, to protect them against copying or imitation, for the authentication of the original containers and of the substance they may contain, for the traceability of the containers and the substance, and for the identification of the container both in the distribution chains and in private use. To solve this problem, this document opts for the initial application of an amount of ink; this is what is engraved with the laser, and then the surplus ink is removed. This entails a weakness in the containers due to the laser marking procedure, and costs due to the excessive consumption of ink. Besides, all the steps necessary for the marking, it being necessary first to apply the ink and then to remove it, generate a very slow marking which affects the production of syringes.

WO2017/048499 A1 discloses a composition of ink employed in a thermal inkjet printer but does not determine any process or printing method by means of the same. In this case, the individual marking directly on the body of the container prior to the labelling stage is not possible; thermal transfer printers are therefore ruled out as they require a support, such as a label, for its marking, and it is this which is affixed to the container.

U.S. Pat. No. 9,662,920 B2 relates to a composition of ink for the printing of a security code on flat surfaces such as labels, boxes or sachets. The ink defined therein for printing comprises an organic solvent, this being between 60% and 90% of the ink by weight, an ink solubilizing agent and two or more different luminescent inks, where each luminescent ink has a different luminescence emission profile; one invisible, which absorbs ultraviolet light, and the other visible. In this case, neither is the pharmaceutical container marked directly, nor is a curved surface marked.

U.S. Pat. No. 5,837,042 A discloses a composition of ink for injection with a fluorescent coloring for printing on white or light-colored objects, specifically for cheques, passports, tickets, certified documents, etc., which bear no relation to the containers of the present invention or the material forming the same.

Finally, U.S. Pat. No. 9,378,445 B2 relates to a method for guaranteeing the authenticity of glass or plastic containers such as syringes, to verify the authenticity of the drugs contained therein. In this case, a 3D code is used, which is marked on the surface of the container, and this is executed by means of a laser, entailing a specific code-reading method for this type of marking. As has been mentioned, the laser printing technique generates microcracks in most of the materials used for the manufacture of the container or syringe, changes in its density or refraction index and small bubbles or hollows in the glass. These microcracks, bubbles or changes in the body of the syringe affect the integrity of the same and cause the marking not to be totally legible; this is therefore not a suitable printing method.

It is therefore necessary to find a marking device and a procedure or method for the marking of syringes suited to enable the correct traceability of the same, and suited to withstand the conditions to which they are subjected; in particular, it must be suited for its application on the customary material of which pharmaceutical containers are manufactured; that is, glass or plastic materials such as polyolefins, without endangering the integrity of the syringes, and it must be rapid, in order not to affect productivity, the marking process or the filling process, and it must overcome the drawbacks of the systems described in the state of the art.

SUMMARY OF THE INVENTION

An object of the present invention is to provide at least one solution to one or more of the above-mentioned problems in the art of container identification, tracking, and serialization.

The present invention provides a marking system for marking container(s), in particular pharmaceutical container(s), with at least one secured identification code (mark), per container, applied directly to said container(s). Said code is either a) not readily visible to the unaided human eye until said code is irradiated with an ultraviolet (UV) or infra-red (IR) radiation thereby creating fluorescence in the visible light spectrum; or b) visible, to a detector, only in the ultraviolet (UV) or infra-red (IR) frequencies of the spectrum.

Said code is formed from at least one security ink, which may be applied using ultra-rapid drying inkjet techniques. The code might initially be invisible (not readily visible) to the human eye. After drying, the security ink(s), forming the code(s) would be either a) visible, to a detection system, only in the ultraviolet (UV) or infra-red (IR) frequencies of the spectrum; or b) would exhibit visible fluorescence when illuminated by UV light, where the incidence of a beam of UV light would cause visible fluorescence induced by the effect of the UV radiation. When UV light is absorbed by the dried ink (of the code), the electrons are temporarily pushed into a greater state of energy, and subsequently said energy is released, the electrons returning to their normal state. It is this released radiant energy, or fluorescence, which may be observed in the visible light spectrum, depending on the material radiated. Thus, the code marked on the body of the same is invisible, except under certain conditions, thus complicating the forgery thereof.

The present system enables the marking of the containers while in motion and can be integrated into the production lines with the high quality and reliability. In some embodiments, the marking system comprises an identification (marking) device for pharmaceutical containers, which device comprises at least one means of marking at least one identification code on each of the containers, characterized in that the device comprises at least one inkjet system configured to print the identification code on at least one surface of the moving container with at least one security ink which exhibits visible fluorescence when radiated with ultraviolet (UV) radiation. In some embodiments, the marking is performed with a security ink which is preferably only visible, to a detection system, in the UV spectrum or the IR spectrum. It is therefore invisible to the human eye.

The security ink exhibits good adherence to refrigerated containers at temperatures of approximately 15° C. and up to ambient temperature, and a very rapid drying time, enabling high operating speeds. The drying time of the ink is about 1 to about 3 seconds, about 1 to about 2 seconds, about 3 seconds or less, about 2 seconds or less, or about 1 second or less.

This system relates preferably to a self-contained identification unit (marking unit) which enables the individual, automated marking of moving pharmaceutical containers of small dimensions with a secured identification (ID) code using inks invisible to the human eye and presenting the characteristic of being heat-resistant and quick-drying.

The marking system and procedure employs security inks that either are only visible in those parts of the light spectrum beyond the spectrum visible by the human eye, such as the ultraviolet spectrum (UV inks) or the infra-red spectrum, or exhibit (emit) visible fluorescence when a beam of UV light is directed thereto (fluorescent inks). In some embodiments, said UV ink must be visible within the wavelength interval of 10 to 400 nm, more preferably within the wavelength interval between 320 and 400 nm, and even more preferably at the wavelength of approximately 365 nm. In preferred embodiments of the invention, the fluorescent ink produces (emits) visible light radiation, when irradiated with an excitation radiation within a UV wavelength of between 10 to 400 nm, between 320 and 400 nm, more preferably approximately 365 nm, is applied thereto.

The security ink(s) usable in the systems and methods of the present invention may also feature one or more of the following desired technical characteristics which can provide additional advantages:

To have quick-drying properties, to prevent the ink from becoming illegible due to smudging during the transport of the containers along the production line, bearing in mind that the speed of the operation may reach 200 units/minute. Ideally, the drying time of the ink is approximately 1 to 3 seconds, preferably 1 to 2 seconds.

To exhibit sufficient adherence to containers at temperatures starting at 15° C., that is, those which require refrigerated storage, up to ambient temperature.

To exhibit resistance to degradation at high temperatures, particularly for those products which require terminal sterilisation; that is, those which are subjected to a radiation or autoclave process at a temperature above 120° C. for at least 20 minutes.

To not interfere with container filling procedures under sterile manufacturing conditions, and to be stable to sterilization conditions.

The types of security ink(s) used according to the invention, as described herein, are used with a device of the invention, without limitation, so as to:

a) unequivocally identify pharmaceutical containers and/or their contents between different stations of a production process prior to labelling, b) to trace the product, for example in third party manufacturing, c) to serialize products and to prevent and/or detect a fraud, possible contamination, an error in a batch, or any other contingency, and d) to identify the drugs and placebos in a clinical trial employing masking techniques in order to prevent the expectations of the patient, the physician/investigator or the evaluator himself from influencing the result observed (see single-blind, double-blind or triple-blind).

Consequently, in a first aspect, the invention is directed toward a marking system (device, apparatus, machine, or equipment assembly) for the identification (marking) of pharmaceutical containers comprising at least one means of marking at least one secured identification code on each of the containers, characterized in that the device comprises at least one inkjet system configured to print said code on at least one surface of said container(s) with at least one security ink which a) exhibits visible fluorescence when radiated with ultraviolet (UV) radiation; or b) is only visible, to a detection system, in the UV or IR light spectrum.

The marking system comprises at least the following operation stations: a) at least one loading station for the insertion of one or more containers into a marking station; b) at least one marking station for marking of said one or more containers with a secured identification code as described herein with a security ink as described herein; c) at least one reading station for reading and verification of said identification code; and d) at least one sorting station for directing said containers to an exit station or to a rejection station. Said operation stations may be integrated into a single machine, device, or apparatus or may be part of an equipment assembly. One or more of said stations is optionally further equipped with at least one detection system ensuring correct operation of its respective station.

In a second aspect, the invention is directed toward a process for the marking (application of unique identifier, e.g. identification code) of pharmaceutical containers with at least one secured identification code on each of the containers, said process comprising the step of printing said identification code by means of an inkjet system on at least one surface of the container with at least one security ink which a) exhibits visible fluorescence when radiated with ultraviolet (UV) radiation; or b) is only visible in the UV or IR light spectrum. Said marking (by printing) can be conducted when respective container(s) is(are) are still or in motion.

The invention also provides a method for marking one or more pharmaceutical containers, said method comprising at least the steps of a) loading said containers at a loading station; b) marking said containers at a marking station to form marked containers, wherein said marking includes printing respective secured identification code(s) on said container(s), wherein said identification code comprises at least one security ink that 1) emits visible fluorescence when irradiated with ultraviolet radiation, or 2) is only visible in the UV or IR light spectrum; c) reading and verifying said identification code(s) at a reading station; and d) sorting said marked containers at a sorting station.

The method optionally further comprises one or more of the following steps: a) detecting the presence of containers at one or more stations; b) halting movement/operation of a container transfer system; c) initiating movement/operation of a container transfer system; d) ejecting said marked containers; e) halting movement/operation of a container transport (conveyor) system; f) initiating movement/operation of a container transport (conveyor) system; g) inverting unmarked containers; h) inverting marked containers; i) turning (rotating) unmarked containers; h) turning (rotating) marked containers; j) applying sealing material to said identification code(s); k) collecting said marked containers.

In some embodiments, the at least one secured identification code is selected from the group consisting of at least one two-dimensional code, QR code, BIDI code, datamatrix code or alphanumeric code. More preferably, the at least one secured identification code is a datamatrix code.

In preferred embodiments, the identification procedure and system for pharmaceutical containers may be applied to different mechanical systems for the handling and transport thereof at the pharmaceutical container filling (with active ingredient(s) or excipients) and corresponding capping/sealing lines. Some of the mechanical systems to which the identification procedure and system described herein may be applied are described below.

In some embodiments, the surface, of the container, being marked is a flat surface or a curved surface.

The invention includes all combinations of the embodiments and subembodiments described herein.

BRIEF DESCRIPTION OF THE DRAWINGS

For the purpose of aiding the better understanding of the characteristics of the invention, in accordance with a preferred example of a practical embodiment of the same, a set of drawings is attached as an integral part of said description wherein, by way of illustration and not limitation, the following is portrayed.

DETAILED DESCRIPTION OF THE INVENTION

Figure 1:
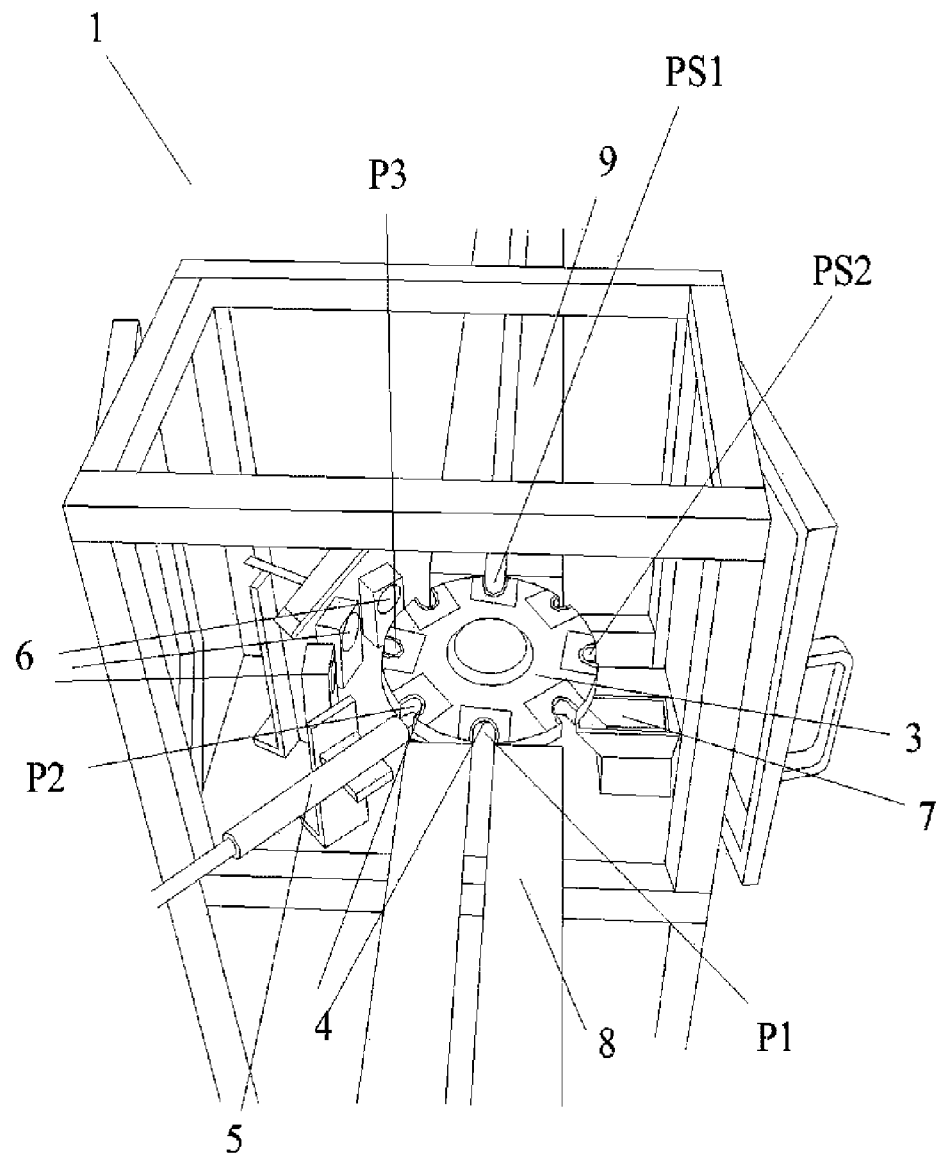
FIG. 1 depicts a perspective view of the station for a preferred embodiment of the invention.
Figure 2:
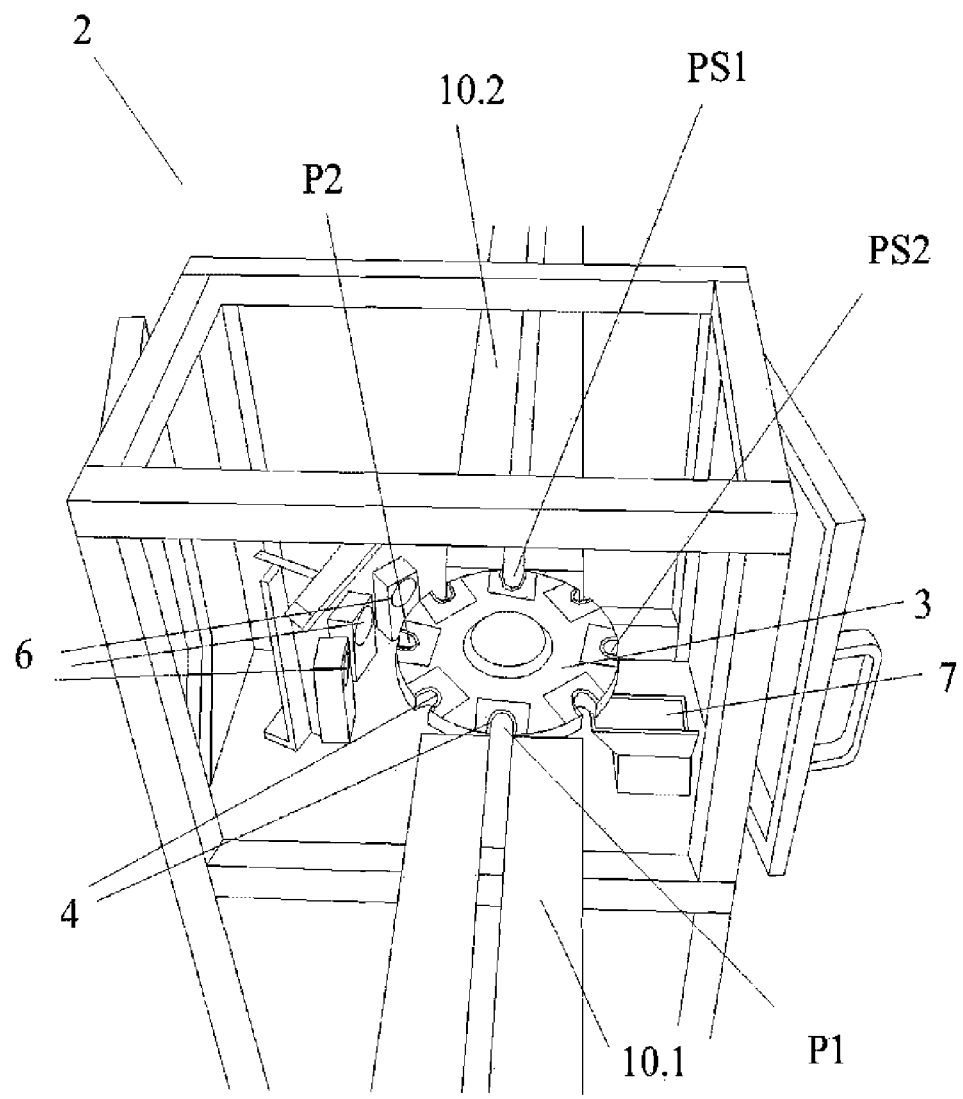
FIG. 2 depicts a perspective view of the additional station, for a preferred embodiment of the invention.

As used herein, "code" is understood to be any industrial two-dimensional encoding system which enables the generation of a large amount of information in a format of reduced size, with highly reliable reading due to its redundant information system and error correction (legible even with 20%-30% damaged), of the datamatrix type, or 2D data encryption. The code consists of black- and white-colored cells forming a square or rectangular figure. Each of these cells represents an information bit. The information may be encrypted as text or raw data. For the object of the invention, the identification code is selected from the group consisting of a two-dimensional code, a QR code, a BIDI code, a datamatrix code or an alphanumeric code, alone or in any combination thereof.

As used herein, "containers" or "pharmaceutical containers of small dimensions" are understood to be those selected from the group consisting of syringes, vials, capsules, ampoules, single-dose devices, inhalers, bottles, cartridges or bags. These containers may be made of glass or of other materials, such as polymers, elastanes, rubbers, polyolefins or other plastic materials. The surface to be marked on said containers may be flat or curved. Said containers may contain liquid, gel, semi-solid or solid substances, e.g. those selected from the group formed by powder, lyophilisates, granules, pellets, nanoparticles or microparticles, whether sterile or not.

It must be borne in mind that the visible portion of the UV spectrum radiates between 400 and 700 nm, and this is the only radiation of the spectrum which can be seen by the human eye. Consequently, a security ink should not be visible in this band of the spectrum. On the other hand, the portion of the UV spectrum which is invisible to the human eye radiates between 10 and 400 nm, and is divided into four regions; the long-wave region, between 320 and 400 nm, the medium-wave region, between 280 and 320 nm, the short-wave region, between 180 and 280 nm, and finally the vacuum region, between 10 and 180 nm. Consequently, in the present invention, the UV ink must emit (exhibit visible fluorescence) within the interval of 10 to 400 nm, more preferably within the interval between 320 and 400 nm, and even more preferably at approximately 365 nm.

In a preferred embodiment, the security ink comprises at least one luminescent colorant, at least one organic solvent and at least one binding resin. Preferably, the luminescent colorant is a sulphonamide, more preferably a toluenesulphonamide, and still more preferably N-ethyl-o(o p)-toluenesulphonamide. This luminescent component may be included in any organic solvent which is compatible with the nature thereof. In preferred embodiments, the solvent is selected from the group consisting of methanol, ethanol, propanol, ketone, ethyl ketone, methyl-ethyl ketone, isopropyl acetate, butanone and 2-pyrrolidone, each alone or in any combination thereof.

Optionally, the security ink may further comprise at least one solubilizing agent, selected from among cyclic ketones, heterocyclic amides, cyclic alcohols and furans.

The printing step (marking) is preferably performed on the container(s), e.g. syringe(s), when they are in motion. "In motion" is to be understood as the movement of the syringes along a production or assembly line, and consequently, this may be between a very slow movement, of several millimeters per minute, and a very rapid movement, of up to 500 meters per minute; more preferably, up to 300 meters per minute.

Datamatrix codes are generally in geometric shapes, e.g. circles, squares or rectangles, measuring about 2 to about 4 mm$^2$ in diameter (width, breadth) and being comprised of individual cells where each represents an information bit. The information is encrypted in a two-dimensional data matrix which can contain a large amount of information, and the data may be encoded as text or as raw data, and may include data such as the identity of the manufacturer, the details of the component marked (including the active ingredient(s) included in the container, and its serial number.

During examination of a marked container, the reading of the secured ID code is performed by means of a camera or reader able to capture the visible light radiation emitted by the secured ID code, so as to subsequently proceed with the reading of the same in accordance with the type of code in question (two-dimensional, QR, BIDI, datamatrix, etc.) and thus to determine its content, which is a numerical or alphanumerical code identifying the pharmaceutical container. To improve the visibility and legibility of the secured ID code, the reading is preferably performed by placing a dark, optimally black, background behind the pharmaceutical container, in such a way that the camera will read the code illuminated against a dark background. In this way, the visibility, and therefore the reading of the code, is optimized, thus preventing errors in the reading thereof. This reading may be performed either on a stationary container or on one which is in motion on the marking line. Optionally, prior to said reading, a stage (step) of cleaning the surface of the container may be included, for the purpose of improving the legibility of the code.

In some embodiments, the system of the invention, which includes the marking and identification system for pharmaceutical containers described herein, comprises the following workstations:

1) A loading station for the insertion of one or more containers into a marking station. In a preferred embodiment, this loading station is implemented in the form of a band or rail, such as an inspection rail, by means of which the container(s) enter(s) the marking station, which consists of a rotating platform or turntable comprising plural receptacles, e.g. cut-outs; the container enters one of the receptacles due to gravity and optionally due to the pressure from the following containers. If necessary, it is possible to use beforehand (upstream of the loading station) a container-turning device (an inverter) to place the container in a perpendicular position, should it not enter in said position. Optionally, a halting device may also be provided to halt the containers, so that they enter the rotating turntable only when pushed by another container, thus preventing the jamming of the system if a container has not correctly entered one of the cut-outs in the rotating platform or turntable. The loading station may optionally be equipped with a container load sensing system which prevents the passage of the containers when there is an insufficient number thereof to ensure sufficient thrust, to prevent them from becoming jammed.

2) A marking station, which performs the marking of the pharmaceutical container, encoding the container disposed on the aforementioned rotating platform or turntable with an identification code by means of ink which exhibits visible fluorescence when irradiated with ultraviolet radiation.

3) A reading station, which includes means for reading and verifying the identification code marked on the container. Said means may be at least one reader such as a camera, to read and verify the identification code encrypted on the container, as a result of which:
   a) if the reading and verification means determine that the encryption is correct, the container is considered suitable, and a sorting device (an actuator, optionally a pneumatic actuator) ejects the container from its cut-out in the turntable and sends it to an exit station, and
   b) if the reading and verification means determine that the encryption is incorrect, the container is considered unsuitable, and said sorting device ejects the container form its cut-out in the turntable and sends it to a rejection station.

The sorting device may be integrated with or separate from the reading station. The sorting device may be part of a sorting station.

At each of these stations, the marking system will preferably be equipped with at least one detection system (detector) to ensure its correct operation. Thus, the system may comprise one or more of the following detection systems, among others, in any combination thereof:

At the container insertion (loading) station, the system further comprises container detection means, preferably photocells, which detect whether there are containers at the marking station, thus to prevent the marking means of the marking station from operating when there are no containers therein;

At the reading station, subsequent to the passage through the reading and verification means, the system further comprises container detection means, such as a photocell, intended for the detection of the presence or absence of the containers at the exit of said station. Should these detection means not detect the presence of a container deemed suitable at the exit station, the system is programmed to halt, as this would mean that suitable containers are being sent to the rejection station instead of to the exit station. A situation of this type, although representing an error, is not considered to be a critical error, as the only practical consequence thereof is that suitable containers are being rejected. For this reason, the system may be programmed so that said halting should not occur after a single isolated error, but when a certain number, by way of illustration, three, consecutive errors of this type should arise. Likewise, should the detection means not detect the presence of a container deemed unsuitable at the rejection station, the system is programmed to halt, as this would mean that unsuitable containers are being sent to the exit station instead of to the rejection station. Given that this situation is considered to be a critical error (unsuitable containers are being sent to the exit station), in this case the system should preferably be configured to be halted subsequent to the first error of this type detected.

As has been stated, all these detection (safety) systems are optional but preferable; it is not necessary for the entirety thereof to be present, as in a given system there may be any combination thereof. However, in the preferred embodiments all of these systems are present.

Various preferred embodiments of the invention are described below, included solely by way of illustration of the possibilities of the invention, which is only limited by the scope of the attached claims.

In one preferred embodiment, this station is equipped with an adjustable support for the reading and verification means which carry out the inspection of the encoded containers.

In another preferred embodiment, the marking system optionally further comprises a container transfer station formed by container grasping and displacement means, constituted by at least one horizontal rotational platform presenting turning means with regard to a central vertical shaft, and presents at its outer area (periphery) adjustment means for the body of a container.

In some embodiments, the container transfer station further comprises, associated with each rotational platform, means for the marking of at least one identification code on each of the containers, as explained above, and reading and verification means in at least some of the same, suited for the detection of the identification code printed thereon. Said reading and verification means at the station comprise a container rejection station with at least one collection container. In accordance with one embodiment, this pharmaceutical container identification device comprises means for the sealing of the identification code ink on the body of the container.

In accordance with another embodiment, the grasping and displacement means of the container transfer station is capable of maintaining the containers in an approximately vertical position during at least part of their travel. In this case, and in an optional embodiment, the grasping and displacement means of the station further comprises a device (an inverter) for upturning (inverting) the containers by 180°.

In accordance with one embodiment, the rotational platform comprises a container rotator, e.g. means for the turning of the containers with regard to the longitudinal axis thereof. These turning means are formed by a motorized band disposed interiorly to the rotational (rotating) platform which, in one embodiment, transmits the turning movement directly to the containers by means of its adjustment to the lower part of the same, while in another embodiment it transmits said movement indirectly to the same, by means of the movement of a number of rollers in contact with the containers.

In accordance with one embodiment, the means for the adjustment of the container body at the outer area of the rotational platform are formed by compartments suited for the coupling of at least the neck of a container in each.

In accordance with another embodiment, the marking means of the station comprise an inkjet printhead associated with each rotational platform, wherein said printhead applies at least one UV ink or at least one fluorescent ink. Given that for its application in the identification of containers it is necessary that the technology should enable the individualized direct marking on the body of the same—even prior to the labelling stage—direct thermal and thermal transfer printers are excluded from the present invention in terms of their use for creating the secured mark, as they require a support, for example a label, for its marking, and subsequently it is the latter which is affixed to a syringe or cartridge.

On the other hand, in one embodiment, the reading and verification means act continuously on all the pharmaceutical containers and are formed by at least one continuous UV code reader and/or at least one UV light source. Normally, these means perform a single capture of the image of the code: a capture wherein they read the complete code and determine whether said code is correct or incorrect. However, depending on the speed of the reading and verification means with regard to the time of exposure of the container to the camera, it would be possible that multiple partial captures of the code might be taken, from which a global (integrated, compound) image of the code could be obtained.

In another embodiment, the reading and verification means act occasionally on a certain number of containers and are formed by a manual scanner with UV illumination.

In accordance with another embodiment, the grasping and displacement means comprise two or more horizontally rotational (rotating, rotatable) platforms, and the marking device, at the entrance to the station, comprises means for the consecutive distribution of the containers to each of the platforms.

In accordance with a preferred embodiment, the at least one identification code is a datamatrix code or an alphanumeric code.

In preferred embodiments, this process for marking comprises a) a first step of inserting into a station a container in a vertical position via a first conveyor belt; b) subsequently, a second step occurs: the grasping said container in the adjustment means of a horizontal rotational platform, by means of the container grasper (container grasping and displacement means) of said station; c) a third step, wherein the platform is turned to a second position to move the container into position printing of the at least one identification code; d) subsequently, a fourth step, consisting of the marking of the containers with at least one identification code by way of a marker (the station marking means); and e) a fifth step of turning the platform until the container reaches an exit position of the same from the station. In an optional embodiment, the step of marking the containers with at least one identification code comprises a finishing step, whereby the ink is sealed onto the body of the container via a sealer (sealing means). Sealing can be accomplished by application of varnish, lacquer, etc., onto the code and container. Sealing is particularly suitable in cases where the container must be subjected to a final sterilization process in the autoclave to prevent possible damage being suffered by the ink due to the material of the container. Alternatively, it is also possible that this finishing step may consist merely of drying of the ink.

In accordance with a preferred embodiment, subsequent to the step of marking with at least one identification code, the procedure may comprise an additional step of verification of the identification code. In this case and in one embodiment, the procedure comprises a step, prior to the additional stage of verification of the identification code, consisting of the turning of platform to move the container from the third position to a fourth position, where said additional stage of verification is performed.

According to one embodiment, prior to the step of marking the containers with at least one identification code, turning comprises a first inverting of the containers by 180°.

Said additional verification stage takes place for each of the containers inserted into the station, where the reading and verification means act continuously or occasionally.

On the other hand, in one embodiment, in the event that subsequent to the verification of the code it is deemed suitable, the platform rotates to move the container to an exit position aligned with a second conveyor belt leaving the station.

Likewise, in the event that the containers have been subjected to a first 180° inversion, the procedure comprises a second 180° inversion of the same to regain their initial position, subsequent to the verification and prior to the turning of the container toward the exit position.

Likewise, in a preferred embodiment, in the event that subsequent to the verification of the code, it may be deemed incorrect, so the platform rotates thereby directing a rejected container toward an exit position aligned with the rejection station collection containers, and the container is ejected by pneumatic or mechanical means into one of said collection containers.

In accordance with one embodiment, when the grasping and displacement means comprise two or more rotational platforms, subsequent to the entry of the container into the station and prior to the grasping of the same by the adjustment means, it comprises an intermediate stage of the consecutive distribution of these containers to each of the rotational platforms by a distributor (distribution means).

In accordance with a preferred embodiment, in the event that the identification code is deemed suitable, the performance of a new inspection step is made possible, either within the internal production line of a company or exteriorly thereto, at a subsequent time during distribution. In this way, subsequent to the displacement of the container to the inspection step, the procedure comprises a series of steps, as follows: a) first, inserting a marked container into an additional station of a container in a vertical position, via a third conveyor belt; b) next, grasping the marked container by the adjustment means of the grasping and displacement means of said additional station; c) then turning the marked container toward a second position wherein the inspection of the identification code and the turning of the container are performed; wherein the inspection at the additional station would be performed on 100% of the containers, in order to prevent cases of cross-contamination; d) next, the procedure presents two possibilities for the fourth step: option 1) the result of the inspection is that the identification code is suitable, in which case the container turns toward an exit position aligned with a fourth conveyor belt for its displacement toward the exterior of the additional station; option 2) the result of the inspection is that the code is incorrect, in which case the container turns toward an exit position aligned with the rejection station collection containers, and the container is ejected by pneumatic or mechanical means into one of said collection containers.

With the device for the identification of pharmaceutical containers and the procedure proposed herein, a significant improvement to the state of the art is obtained.

This is so, as a pharmaceutical container identification device is obtained whereby a marking on the body itself of containers of small dimensions and made of any material, whether glass or plastic material, is enabled; and where the device integrates all the necessary parts in a compact piece of equipment; that is, it integrates the marker (marking means) and the verifier (reading and verification means) into a modular piece of equipment which can easily be included at any point in the production line; it can therefore be installed at that point of the line where a need for verification arises, in accordance with the peculiarities of the different production lines existing in the market.

It is therefore possible to locate the system downstream of the container packing and capping stage, in such a way that a correct identification of both the container and its content is ensured during the entire remainder of the production process, preventing errors in the identification of the containers then and subsequently, once in the market, thus preventing the possible counterfeiting of drugs during the distribution stage, and also possible errors of identification.

Besides, in the event that an identification device installed at a point in the production line should present an operation problem, as it is totally modular it is possible to remove it from the line, so that production may continue independently of this device, until it can be repaired.

The marking system (marking device) is configured as a compact item of equipment which is sufficiently robust to provide the containers with the necessary stability during the movement thereof. This device is able to perform the marking of any material, on flat or curved surfaces, more rapidly, with increased efficacy and while reducing the risk of breakages during handling and thereby ensuring the aseptic environment of the process.

Furthermore, this would preferably be a totally automated process, where personnel have no contact with the containers during operation, therefore being hygienic and predictable, as it does not depend on the human factor.

It is therefore a very efficient identification device and procedure, usable at both the internal production level and at the time of distribution, enabling the monitoring of the traceability of the pharmaceutical containers, providing safety and reliability to the drugs, enabling on the one hand greater internal control in pharmaceutical companies by facilitating the identification of their product from the moment when it is packed, preventing possible errors or confusion in the same, and on the other hand, preventing counterfeiting and possible errors of identification of the drugs, as it is also possible to verify the code subsequent to manufacture, at the distribution or sales centers. Preferably, the procedure is characterized in that it is performed under sterile conditions.

The device of the present invention and the procedure for the performance of the same are preferably configured for syringes, generally glass or plastic syringes for pharmaceutical use, preferably for sterile injectables.

DETAILED DESCRIPTION OF A PREFERRED EMBODIMENT OF THE INVENTION

In view of the figures provided, it may be observed how, in a preferred embodiment of the invention, the device (system, 1) of the invention for the marking of syringes proposed herein comprises syringe grasper (grasping and displacement means), marker (means for the marking of at least one identification code on each of the syringes), and verifier (means for reading and verification of the secured identification code of at least some of the syringes), and detector (means for detecting the secured identification code printed thereon).

Accordingly, the overall marking system of the invention comprises at least one container grasping and displacement system, at least one marker, at least one reading and verification system, and at least one detection system. In some embodiments, a marker is a printer.

In a preferred embodiment of the invention and in reference to a container handling process equipment assembly, the marking system is located between the syringe filling and capping station and the inspection station, in such a way that a perfect traceability of the production process thereof may be achieved. On the other hand, the at least one identification code is a datamatrix code, which, due to it being a two-dimensional code, enables the inclusion of a great amount of information in a format of reduced size, and the redundant information included presents high reading reliability. Therefore, due to the limitations of the space existing for the marking of the smaller syringes, and to the high speed at which they are processed, the datamatrix code presents advantages in comparison with the alphanumeric code.

At the station (1) the syringe grasping and displacement means is adapted to maintain syringes in a generally vertical position during their entire travel. Additionally, in other embodiments, the grasping and displacement means of the station may further comprise a device for the inverting the containers by 180°.

As portrayed in FIG. 1, said grasping and displacement means comprises a horizontal rotational platform (3) which presents means for its turning (rotating, spinning) around (about) a central vertical shaft, and respectively presents at its external area (extremity) adjustment means for the body of a syringe.

Thus, in other embodiments, in the event of a greater speed of the production line, two or more rotational (rotating) platforms may be used; in which case, each would be associated with a marking means and a reading and verification means, respectively.

In this preferred embodiment of the invention, the identification code is initially invisible to the human eye, and said marking means comprises a UV inkjet printhead (5) associated with said rotational (rotating) platform (3). The marking device further comprises at least one code sealing station comprising a sealer (means, not portrayed in the figures, for sealing of the ink to the body of the syringe), as discussed above.

Thus, in this preferred embodiment, the verifier (reading and verification means) acts continuously on 100% of the syringes, and comprises two UV light sensitive cameras (6). Normally, these means perform a single capture of the image of the code: an image capture wherein they read the complete code and determine whether said code is correct or incorrect. However, depending on the speed of the reading and verification means with regard to the time of exposure of the container to the camera, it is possible that alternatively, multiple partial captures of the code might be taken, from which a global (compound or integrated) image of the code is obtained (or prepared). In this preferred embodiment, the number of code readers or cameras is two; one of these is assigned to perform a first attempt to read the code on a particular container, an attempt which is usually successful; followed by a second reader or camera, assigned to perform the reading of those codes which could not be read correctly at the first attempt, for example because at the first attempt the reader or camera was not correctly facing the code. Alternatively, to ensure that the reading of the code is performed correctly, whether at the first or second attempt, it is possible to include a greater number of cameras, for example four cameras facing each other, configured to be able to read the code at any point of the 360° circumference around the container. In this last case, the lighting should come preferably from the exterior to prevent the light from one camera or reader from adversely affecting the camera/reader opposite.

When performing the verification of 100% of the syringes, it is possible to know whether the printhead (5) is operating correctly, it being possible to halt the marking device in the event that consecutive faults be detected, to resolve the problem.

In this preferred embodiment of the invention, given the speed of the line, the grasping and displacement means comprises a single rotational (rotating) platform (3).

Also, the reading and verification means of the station (1) comprises a rejection station with at least one syringe collection container (7, rejection station) for those where the identification code is incorrect or defective.

In this preferred embodiment of the invention, the horizontal rotational platform comprises a turning means for the syringes with regard to the longitudinal axis thereof, formed by a motorized band disposed interiorly to the rotational (rotating) platform (3) which transmits the turning movement directly to the syringes by means of adjustment to the lower part of the same.

In other embodiments, these means for turning the syringes may be formed by a motorized band disposed interiorly to the rotational platform which transmits the turning movement indirectly to the syringes via the movement of a number of rollers in contact therewith. At the same time, these rollers provide the syringes with stability.

In this preferred embodiment of the invention, the means for adjusting the body of a syringe at the outer area of the rotational platform (3) are formed by grasping compartments (4) which are adapted to couple at least the neck of a syringe in each. These grasping compartments (4) may hold the syringe by the neck or by a larger area thereof.

In this preferred embodiment of the invention, the UV ink is visibly luminescent under a UV excitation light within the range between 320 and 400 nm. Thus, this UV ink comprises at least one organic solvent, at least one binding resin, at least one luminescent colorant, and at least one solubilizing agent selected from among cyclic ketones, heterocyclic amides, cyclic alcohols and furans.

In order to arrive at the solution (invention) disclosed herein, a prior study was performed wherein the following were taken as fundamental premises:

The syringes arrive at the marking device in a vertical position, held by the neck, and must be passed by the marking device to the next item of equipment in the same position.

The syringes arrive with no minimum separation between them.

The syringes are marked on the body thereof and may be of different sizes and materials.

It is necessary to have collection containers (7) for the collection of the syringes which the inspection device deems unsuitable, either because the information contained in the datamatrix code does not coincide, due to a printing error, or to an error in the inspection.

This collection container (7) must be disposed in such a way that it is not possible to handle and/or extract syringes prior to their ejection, as this would cause errors in the rejection. Furthermore, it must be disposed so that the syringes are not damaged when they fall, as those which are rejected incorrectly (false rejection) or due to defective printing should be reprocessed.

The speed at which the syringes are to be processed depends on the speed of the production line.

Bearing in mind this information, during the prior study different container transporting systems were considered, in order to develop optimal, appropriate grasping and displacement means:

Test 1 Transport in a Horizontal Position

In this case, the syringes, which were initially in a vertical position and with no separation between them, are sent along a conveyor belt system which turns them 90° and also establishes a separation between them.

The printing and verification is performed in a horizontal position in the event of exiting the packing and capping stage, and the inspection alone in the event of inspection prior to the labelling stage. Subsequent to the inspection, the syringes not deemed suitable are rejected pneumatically, while those deemed suitable pass on to a group of bands which turn them 90° and arrange them in a vertical position once more.

This solution provides the syringes with sufficient stability for the printing and initial verification at the exit from the packers. However, in the inspection prior to entry into the labelling machine, where the mark may be at any point of the body of the syringe (360°), it is necessary to rotate them, as only part of the same is visible, which increases the complexity due to the syringes being in a horizontal position. For this reason, this solution was rejected.

Test 2 Transport in a Vertical Position Via a Band System.

In this case, the syringes enter the marking device via a worm drive or similar equipment, which establishes a minimum separation between them. Within the device, they are transported in a vertical position, where they are held by the neck by means of a lateral band system. They are marked laterally and are verified in the case of exiting the packing and capping stage or are only inspected in the case of inspection prior to entry into the labelling stage.

Subsequent to inspection, the syringes not deemed suitable are rejected pneumatically, while those accepted are passed to a longitudinal conveyor belt which carries them, held by the neck, to the next item of equipment.

The grasping of the syringes only by the neck causes them not to be sufficiently stable, especially during the printing at the exit from the packing and capping stage. Furthermore, transport via longitudinal belts makes necessary the use of at least four cameras for the inspection prior to the labelling stage, to ensure the visibility of the mark which may be on any part of the body of the syringe. These must be facing each other in order to perform the inspection correctly, which may cause the light from some to affect the others. For these reasons, this option was rejected.

Test 3 Transport in a Vertical Position Via a Rotational Platform.

The syringes, transported in a vertical position and held by the neck, are inserted into a rotational (rotating) platform, in such a way that a minimum distance is established between them. This system rotates, causing the syringes, which themselves do not rotate, to pass through four positions:

Position 1: the printing is performed in the case where the equipment is disposed subsequent to the packing and capping stage. The equipment assigned for action prior to the labelling stage does not feature the option of printing.

Position 2: the verification or inspection is performed, according to which equipment.

Position 3: the accepted syringes are delivered to a longitudinal conveyor belt leading to the next item of equipment.

Position 4: the rejected syringes are ejected pneumatically into a rejection container, e.g. box.

As in the previous case, the grasping of the syringes only by the neck causes them not to be sufficiently stable, especially during the printing at the exit from the packing and capping stage. Furthermore, prior to the labelling stage, as the mark may be on any part of the bodies of the syringes, and given that these do not themselves rotate, it is necessary to integrate a viewing system comprised of at least four cameras facing each other, entailing the possibility that the light from some may affect the others. For these reasons, this option is rejected.

Test 4 Transport in a Vertical Position Via a Platform Where the Syringes May Rotate.

This solution is similar to the previous one, with the difference that the syringes, in addition to being held by the neck in the rotational platform (3), feature a grasping means at the lower part thereof, which causes them to rotate themselves (motorized band). Thus, the stability of the syringes during transport is increased and the problem of light interference among the cameras employed for the inspection is eliminated. Therefore, this is the preferred alternative.

This specification thus presents a procedure for the marking of syringes by means of a marking device as defined herein.

Figure 3:
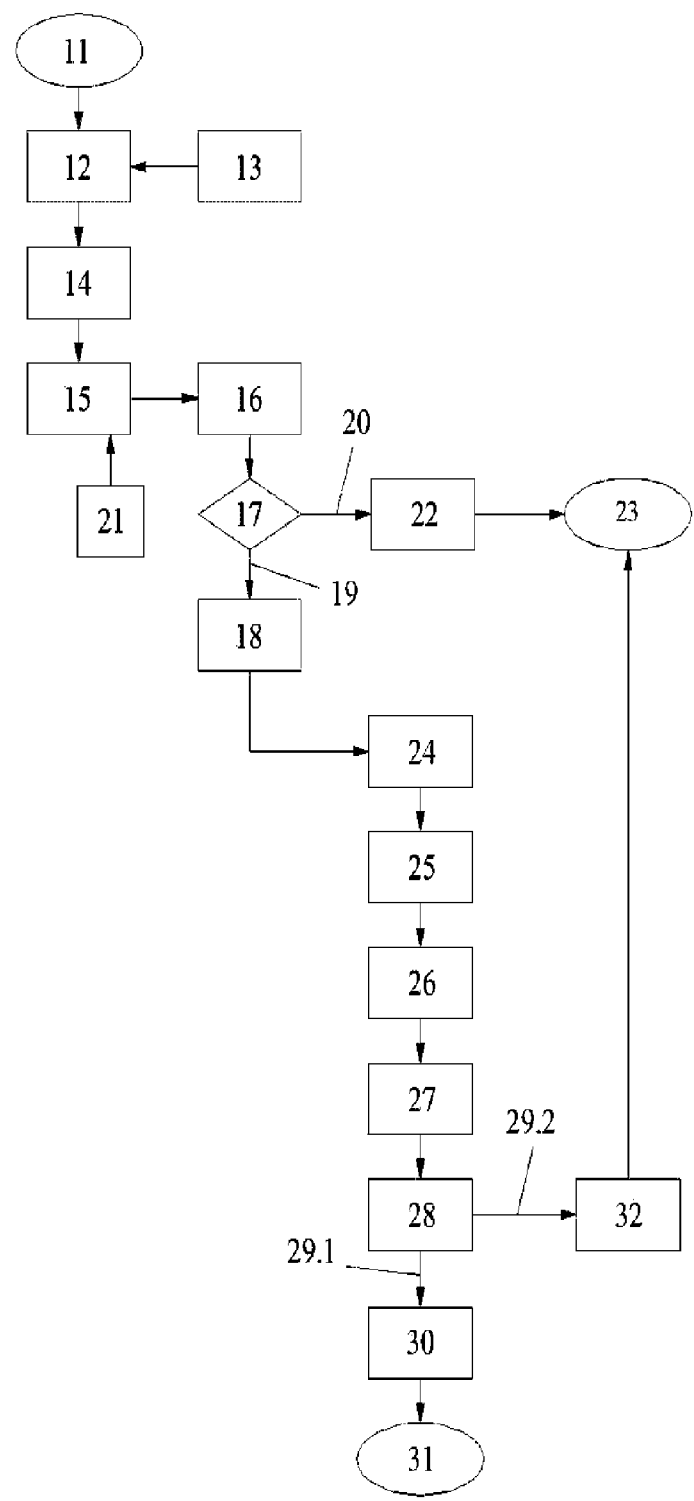
FIG. 3 depicts a block diagram of the procedure for the identification of pharmaceutical containers by means of a marking device as described for a preferred embodiment of the invention.

As portrayed in FIG. 3, this procedure comprises a first stage of inserting, into a station (1), a syringe (11) in a vertical position via a first conveyor belt (8).

Subsequently, the second stage consists of grasping (12) said syringe in the adjustment means of a horizontal rotational (rotating) platform (3) of the syringe grasping and displacement means of said station (1). In this preferred embodiment of the invention, the syringe adjustment means is formed by a compartment (4) at the outer area (periphery) of the rotational platform (3), as may be observed in FIG. 1.

Thus, in this second stage of grasping (12) the syringe, the coupling (13) of the syringe neck in said compartment (4) is performed, as is the grasping of the lower part of the same by means of a motorized band (not portrayed in the figures) which generates a rotating movement of the syringe with regard to the longitudinal axis of the same. Said compartment (4) is located at a first entry position (P1).

The rotational platform (3) can be different for (customized to) each syringe format (type) and features defined (complementarily shaped) grasping compartments (4), in such a way that it establishes a minimum separation between syringes.

Next to occur is the fourth stage, wherein a rotation (14) of said grasping compartment (4) is produced as far as a second position (P2) for the printing, in this embodiment, of at least one invisible identification code, in this case preferably a datamatrix code. In this preferred embodiment of the invention, the equipment features a double-blind system; that is, two different persons will enter the information to be contained in the datamatrix code to be printed, to ensure that this information is entered correctly.

As portrayed in FIG. 3, the fifth stage consists of the marking (15) of the syringes with said identification code, a datamatrix code, by means of the marking means of the station.

In this preferred embodiment of the invention, the stage of marking (15) the containers with at least one invisible identification code comprises a finishing stage, formed by the sealing (21) of the ink on the body of the syringe.

Likewise, in this preferred embodiment of the invention, subsequent to the stage of marking (15) the syringes with an invisible identification code, the procedure comprises an additional stage of verification (17) of the invisible identification code. It likewise comprises a stage prior to said additional stage of verification (17) of the identification code, consisting of the turning (16) of the syringe from the second position (P2) to a third position (P3), where said additional stage of verification (17) is performed.

In other embodiments, it is possible that the additional verification stage (17) may be performed at the same second position (P2) where the syringe marking stage (15) is performed; thus, no rotation of the syringes occurs to any third position (P3) for the performance of the additional verification stage (17).

Given that in this embodiment the reading and verification means act continuously, this second additional verification stage (17) takes place for each and every one of the syringes.

In this preferred embodiment of the invention, the syringes are maintained vertical during the entire process, but in other embodiments it is possible that prior to the stage of marking (15) the syringes with at least one identification code, the syringes may be first upturned (inverted) by 180°. In this case, it is necessary that subsequently a second upturning (inversion) of the syringes by 180° be performed to regain their initial position, subsequent to the verification (17) and prior to the rotation (18) of the syringe toward the exit position (PS1).

Finally, once the identification code has been printed on the body of the syringe, and the verification (17) of the same has been performed by the reading and verification means, the sixth stage is performed, wherein the rotation of the grasping compartment (4) toward a position for the exit of the syringes from the station (1) takes place.

In the event where subsequent to said additional verification stage (17) the code is deemed suitable (19), the syringe grasping compartment (4) rotates (18) toward an exit position (PS1) aligned with a second conveyor belt (9) leaving the station.

On the other hand, in the event that the code is deemed unsuitable (20), the syringe grasping compartment (4) rotates (22) toward an exit position (PS2) aligned with the collection containers (7) and the syringe is ejected (23) by pneumatic or mechanical means into one of said collection containers (7).

In this preferred embodiment of the invention, in the case where the identification code is deemed suitable (19), the existence of a new inspection stage is considered, which in this case is performed within the internal production line of a company, due to the fact that in this case, when passing from one item of equipment to another, the syringes are stored on a tray; therefore a new verification of the same is understood to be necessary. In other cases, this inspection stage may be performed externally from the manufacture of syringes, that is, during the distribution, transport or sales process.

Therefore, a new verification of the invisible identification code on the syringes is performed in order to prevent possible errors, in such a way that an additional module is installed, consisting of a station identical to the first, but wherein only the inspection of the syringes is performed and in this case no marking is carried out. This new inspection may also be performed, as mentioned above, outside the company, by the end client, the hauler, the party in charge of distribution.

In this way, subsequent to the displacement of the syringe to the inspection stage, the procedure comprises a series of stages, as follows:

First, a first stage of the insertion (24) into an additional station (2) of a syringe in a vertical position, via a third conveyor belt (10.1).

Next, a second stage of grasping (25) the syringe by the adjustment means of the syringe grasping and displacement means of said additional station (2) takes place. Given that in this embodiment the adjustment means are formed by grasping compartments (4) at the outer area (periphery) of the rotational platform, in said second stage the coupling (26) of the syringe neck in said grasping compartment (4) is performed, as is the grasping of the lower part of the same by means of a motorized band (not portrayed in the figures). By means of this motorized band, a rotational movement of the syringe is generated with regard to the longitudinal axis thereof. Said compartment (4) is located at a first entry position (P1).

As portrayed in FIG. 3, the third stage is the rotation (27) of said grasping compartment (4) toward a second position (P2) wherein the inspection (28) of the invisible identification code and the rotation of the syringe by the turning means are performed.

In this case, the inspection (28) at the second station (2) is that which is performed prior to the entry of the syringes into the labelling stage, and in this case it is necessary to verify that 100% of the syringes to be labelled belong to the corresponding batch and packing code, in order to prevent cases of cross-contamination.

As the syringes themselves rotate due to the turning movement generated by the motorized band, it is possible to employ continuous datamatrix code readers and cameras able to construct a global (integrated, compound) image from multiple captures, in both cases with UV light. The use of one type or the other is determined by the speed at which the information must be processed. In this preferred embodiment of the invention, it has been decided to employ three cameras (6) to capture images of the moving syringe, both in displacement and rotationally, and to construct the global image wherein the mark to be verified appears.

In this preferred embodiment of the invention, on reaching this point, the procedure presents two possibilities for the fourth stage, the first being that the result of the inspection is that the identification code is suitable (29.1), and the second, that the result of the inspection is that the code is incorrect (29.2).

As portrayed in FIG. 3, when the result of the inspection is that the code is suitable (29.1), the grasping compartment (4) rotates (30) toward an exit position (PS1) aligned with a fourth conveyor belt (10.2) for its displacement to a subsequent stage of the production process, and the transfer (31) of the syringe in a vertical position to said fourth conveyor belt (10.2) takes place.

On the other hand, when the result of the inspection is that the code is unsuitable (29.2), the syringe grasping compartment (4) rotates (32) toward an exit position (PS2) aligned with the collection containers (7) of the rejection station, and the syringe is ejected (23) by pneumatic or mechanical means into one of said collection containers (7).

The embodiment described constitutes solely an example of the present invention, and therefore, the specific details, terms and phrases employed in the present specification should not be considered limitative, but should be understood solely as a basis for the claims and a representative basis to provide a description and sufficient information for the expert skilled in the art to put this invention into practice.

With the syringe marking device and the marking procedure by means of the same presented herein, significant improvements regarding the state of the art are achieved.

A marking device is achieved by which the drug is identified from the packing thereof until it reaches the patient, thus providing safety in the same, by achieving control over the traceability of the syringes both at an internal level at the production line and at the level of the distribution thereof.

This marking device enables the printing of an identification code on the body of the container itself, be it made of glass or plastic and of any size, this code also being invisible, therefore not affecting the appearance of the syringe or other markings it might bear.

In addition, the marking device is (can be) integrated in a compact, modular station which integrates the marking and verification means, being sufficiently robust to provide the necessary stability to the syringes during their displacement.

In addition to providing greater safety to the process, this enables a greater speed of the same, enabling the obtaining of greater productivity.

Furthermore, due to it being a modular station, it may be installed at the location of the production line where it may be required, according to the particular requirements of that line, or even outside the production line, at the distribution centers or sales centers, thus providing correct, safe traceability for these syringes.

On the other hand, the secured identification code is initially invisible to the human eye and can only be viewed in the UV spectrum, thus making any possible counterfeiting more difficult.

This is a simple marking device and procedure which is highly effective in the marking and traceability of syringes, without the intervention of the human factor, thus reducing possible failures due thereto.

The invention claimed is:

1. A marking system for marking pharmaceutical containers with at least one secured identification code, said system comprising at least one container marker that applies at least one said code to said containers, said code being formed from of at least one security ink and said code being either a) not readily visible to the unaided human eye until said code is irradiated with an ultraviolet (UV) or infra-red (IR) radiation thereby creating fluorescence in the visible light spectrum; or b) visible only in the ultraviolet (UV) or infra-red (IR) frequencies of the spectrum;
wherein said system comprises at least the following operation stations: a) at least one loading station for the insertion of one or more containers into a marking station; b) at least one marking station for marking of said one or more containers with a secured identification code as described herein with a security ink as described herein to form marked containers; c) at least one reading station for reading and verification of said identification code on said marked containers; and d) at least one sorting station for directing said marked containers to an exit station or to a rejection station; and
wherein said system further comprises i) a rotating platform or turntable comprising plural receptacles; ii) an inverter upstream of the loading station; iii) a halting device to halt loading of said containers; iv) a container load sensing system; v) container detection means; vi) a container transfer station; and/or vi) a code sealing station.

2. The marking system of claim 1, wherein said system comprises at least one inkjet system configured to print said at least one code on at least one surface of said container(s) with said at least one security ink.

3. The system of claim 1, wherein a) said reading station comprises reading and verification means; and/or b) said at least one marking station comprises one or more inkjet printheads.

4. The system of claim 1, wherein a) said loading station loads containers onto said rotating platform or said turntable; b) said reading and verification means comprises at least one camera, at least one UV code reader, and/or at least one UV light source; c) said sorting station is integrated with said reading station; d) said reading and verification means is equipped with an adjustable support; e) said container transfer station comprises container grasping and displacement means; f) said rotating platform or turntable further comprises container rotator; g) said reading and verification means captures one or more images of said code on one or more respective marked containers or on all marked containers; and/or h) the system comprises at least two reading stations.

5. The system of claim 4, wherein said container grasping and displacement means comprises two or more horizontally rotational (rotating, rotatable) platforms and comprises means for the consecutive distribution of the containers to each of said platforms.

6. The system of claim 1, wherein said stations are integrated into a single machine, device, or apparatus, are part of an equipment assembly.

7. The system of claim 1 further comprising at least one detection system.

8. The system of claim 1, wherein said at least one security ink a) exhibits good adherence to refrigerated containers at temperatures of approximately 15° C. and up to ambient temperature; b) exhibits a drying time of about 3 seconds or less; c) is an UV ink visible within the wavelength interval of about 10 to about 400 nm; d) is a fluorescent ink that emits visible light radiation, when irradiated with an excitation radiation within a UV wavelength of within about 320 to about 400 nm; e) exhibits resistance to degradation when exposed to a temperature above 120° C. for at least 20 minutes; f) comprises at least one luminescent colorant and at least one solvent; g) comprises at least one solvent; h) comprises at least one solubilizing agent; and/or i) comprises at least one binding resin.

9. The system of claim 1, wherein said secured identification code is selected from the group consisting of two-dimensional code, QR code, BIDI code, datamatrix code, and alphanumeric code.

10. The system of claim 1, wherein said secured identification code comprises information that is encrypted or encoded.

11. The system of claim 1, wherein said pharmaceutical container is selected from the group consisting of syringe, vial, capsule, ampoule, single-dose device, inhaler, bottle, cartridge, and bag.

12. A method for marking one or more pharmaceutical containers, said method comprising at least the steps of
a) loading one or more containers onto a first rotating platform of a loading station, wherein said platform is in a first position;
b) grasping said one or more containers with container grasping and displacement means;
c) rotating said platform to move said one or more containers to a second position;
d) marking said one or more containers with one or more secured identification codes to provide respective one or more marked containers; and
e) rotating said platform to move said one or more marked containers to an exit position.

13. A method of marking pharmaceutical containers with at least one secured identification code, said process comprising the step of printing said identification code by means of an inkjet system on at least one surface of said containers with at least one security ink which a) exhibits visible fluorescence when radiated with ultraviolet (UV) radiation; or b) is only visible in the UV or IR light spectrum, wherein a) said marking is conducted while said containers are still or in motion; b) the method further comprises the step of sealing said secured identification code(s) onto said marked container(s); c) the method further comprises the step of verifying said secured identification code(s); d) the method further comprises rotating said platform to move said one or more marked containers and verifying said secured identification code(s); e) the method further comprises inverting said one or more containers prior to said marking; f) said loading is conducted with a conveyor; g) the method further comprises the step of unloading said one or more marked containers; h) the method further comprises inverting said one or more marked containers; i) said one or more marked containers are unloaded onto a conveyor; j) the method further comprises rotating said platform to move rejected marked containers to an exit position aligned with a rejection station; k) the method further comprises transferring said one or more marked containers to a second rotating platform; l) the method further comprises inspecting said marked containers on said second rotating platform; m) the method further comprises ejecting rejected marked containers into one or more collection containers; n) said process is performed in a sterile environment; and/or o) the method further comprises halting operation of said system in direct or indirect response to an error detected on said marked container(s).

14. The method of claim 13, wherein said secured identification code is selected from the group consisting of two-dimensional code, QR code, BIDI code, datamatrix code, and alphanumeric code.

15. The method of claim 13, wherein said secured identification code comprises information that is encrypted or encoded.

16. The method of claim 13, wherein said pharmaceutical container is selected from the group consisting of syringe, vial, capsule, ampoule, single-dose device, inhaler, bottle, cartridge, and bag.

17. A method of marking pharmaceutical containers with at least one secured identification code, said process comprising the step of printing said identification code by means of an inkjet system on at least one surface of said containers with at least one security ink which a) exhibits visible fluorescence when radiated with ultraviolet (UV) radiation; or b) is only visible in the UV or IR light spectrum, said method further comprising one or more of the following steps: a) detecting the presence of containers at one or more stations; b) halting movement/operation of a container transfer system; c) initiating movement/operation of a container transfer system; d) ejecting said marked containers; e) halting movement/operation of a container transport (conveyor) system; f) initiating movement/operation of a container transport (conveyor) system; g) inverting unmarked containers; h) inverting marked containers; i) turning (rotating) unmarked containers; h) turning (rotating) marked containers; j) applying sealing material to said identification code(s); and/or k) collecting said marked containers.

18. The method of claim 17, wherein said secured identification code is selected from the group consisting of two-dimensional code, QR code, BIDI code, datamatrix code, and alphanumeric code.

19. The method of claim 17, wherein said secured identification code comprises information that is encrypted or encoded.

20. The method of claim 17, wherein said pharmaceutical container is selected from the group consisting of syringe, vial, capsule, ampoule, single-dose device, inhaler, bottle, cartridge, and bag.

21. A method of marking pharmaceutical containers with at least one secured identification code, said process comprising the step of printing said identification code by means of an inkjet system on at least one surface of said containers with at least one security ink which a) exhibits visible fluorescence when radiated with ultraviolet (UV) radiation; or b) is only visible in the UV or IR light spectrum, wherein said at least one security ink a) exhibits good adherence to refrigerated containers at temperatures of approximately 15° C. and up to ambient temperature; b) exhibits a drying time of about 3 seconds or less; c) is an UV ink visible within the wavelength interval of about 10 to about 400 nm; d) is a fluorescent ink that emits visible light radiation, when irradiated with an excitation radiation within a UV wavelength of within about 320 to about 400 nm; e) exhibits resistance to degradation when exposed to a temperature above 120° C. for at least 20 minutes; f) comprises at least one luminescent colorant and at least one solvent; g) comprises at least one solvent; h) comprises at least one solubilizing agent; and/or i) comprises at least one binding resin.

22. The method of claim 21, wherein said secured identification code is selected from the group consisting of two-dimensional code, QR code, BIDI code, datamatrix code, and alphanumeric code.

23. The method of claim 21, wherein said secured identification code comprises information that is encrypted or encoded.

24. The method of claim 21, wherein said pharmaceutical container is selected from the group consisting of syringe, vial, capsule, ampoule, single-dose device, inhaler, bottle, cartridge, and bag.

* * * * *